US006254642B1

United States Patent
Taylor

(10) Patent No.: US 6,254,642 B1
(45) Date of Patent: Jul. 3, 2001

(54) PERORALLY INSERTABLE GASTROESOPHAGEAL ANTI-REFLUX VALVE PROSTHESIS AND TOOL FOR IMPLANTATION THEREOF

(76) Inventor: Thomas V. Taylor, Veterans Affairs Medical Center 2002 Holcombe Blvd., Houston, TX (US) 77030-4298

( * ) Notice: Subject to any disclaimer, the term of this patent is extended or adjusted under 35 U.S.C. 154(b) by 0 days.

(21) Appl. No.: 08/987,693

(22) Filed: Dec. 9, 1997

(51) Int. Cl.[7] ............................... A61F 2/04; A61F 2/24
(52) U.S. Cl. ............................ 623/23.64; 623/2.1
(58) Field of Search .................... 623/12, 2, 11; 606/151, 108, 153, 154, 215

(56) References Cited

U.S. PATENT DOCUMENTS

| 3,574,865 | * | 4/1971 | Hamaker | 623/2 |
| 4,846,836 | * | 7/1989 | Reich | 623/11 |
| 5,006,106 | * | 4/1991 | Angelchik | 600/37 |
| 5,234,447 | * | 8/1993 | Kaster et al. | 606/153 |
| 5,306,300 | * | 4/1994 | Berry | 623/11 |
| 5,314,473 | * | 5/1994 | Godin | 623/12 |
| 5,411,552 | * | 5/1995 | Andersen et al. | 623/2 |
| 5,861,036 | * | 1/1999 | Godin | 623/12 |
| 5,871,536 | * | 2/1999 | Lazarus | 623/1 |

* cited by examiner

Primary Examiner—Dinh X. Nguyen
Assistant Examiner—Alvin Stewart
(74) Attorney, Agent, or Firm—Daniel N. Lundeen

(57) ABSTRACT

Disclosed is an instrument, valve prosthesis and procedure for the minimally invasive implantation of an anti-reflux valve in a patient for the treatment of gastroesophageal reflux disease. Self-anchoring or stapleable one-way anti-reflux valve prostheses are provided, which may be implanted proximate a patient's gastroesophageal junction without open or laparoscopic surgery. An instrument for the peroral insertion, positioning and fixing of the valve prosthesis to the tissue of the esophagus is described for the implantation of either the self-anchoring or stapleable prosthesis.

17 Claims, 8 Drawing Sheets

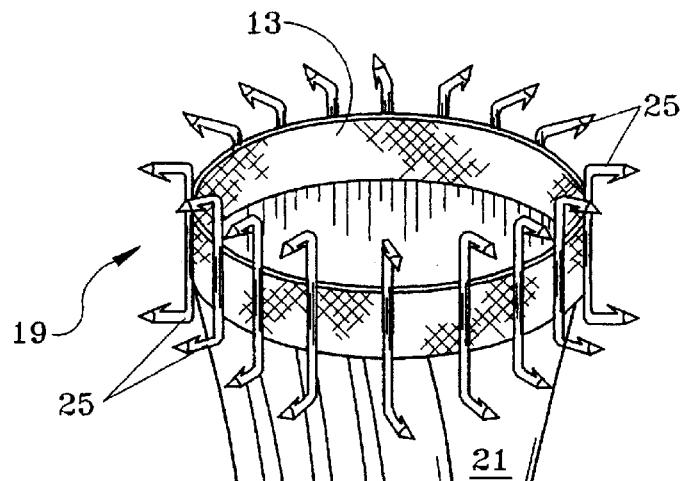
FIG.2B
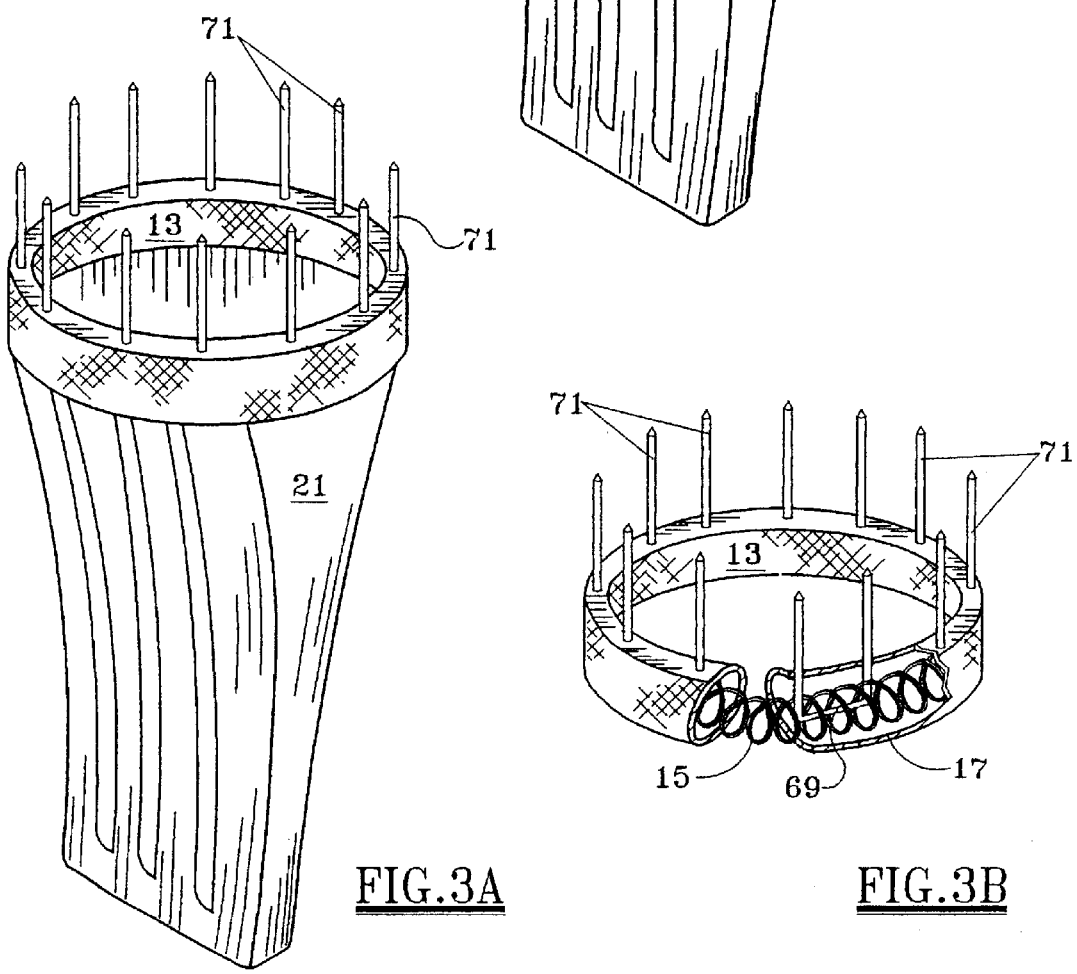
FIG.3A
FIG.3B

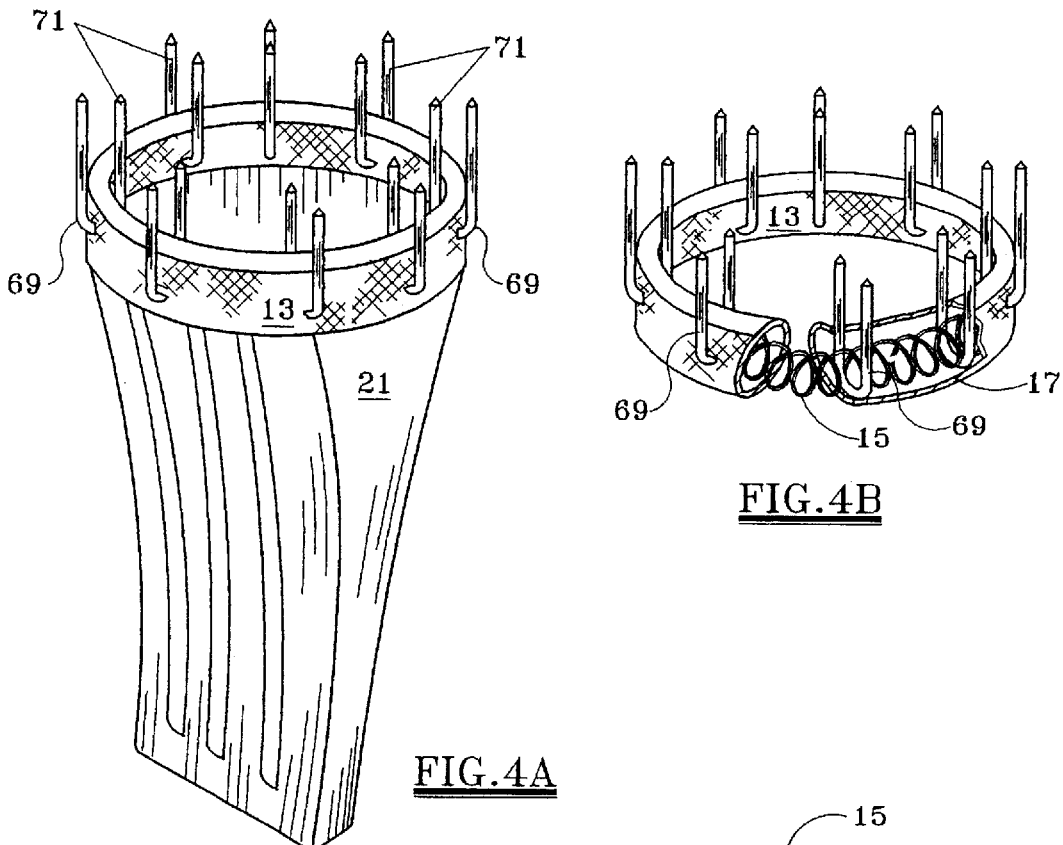
FIG.4B
FIG.4A
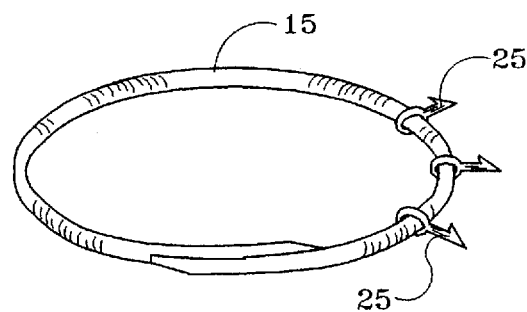
FIG.5A
FIG.5B

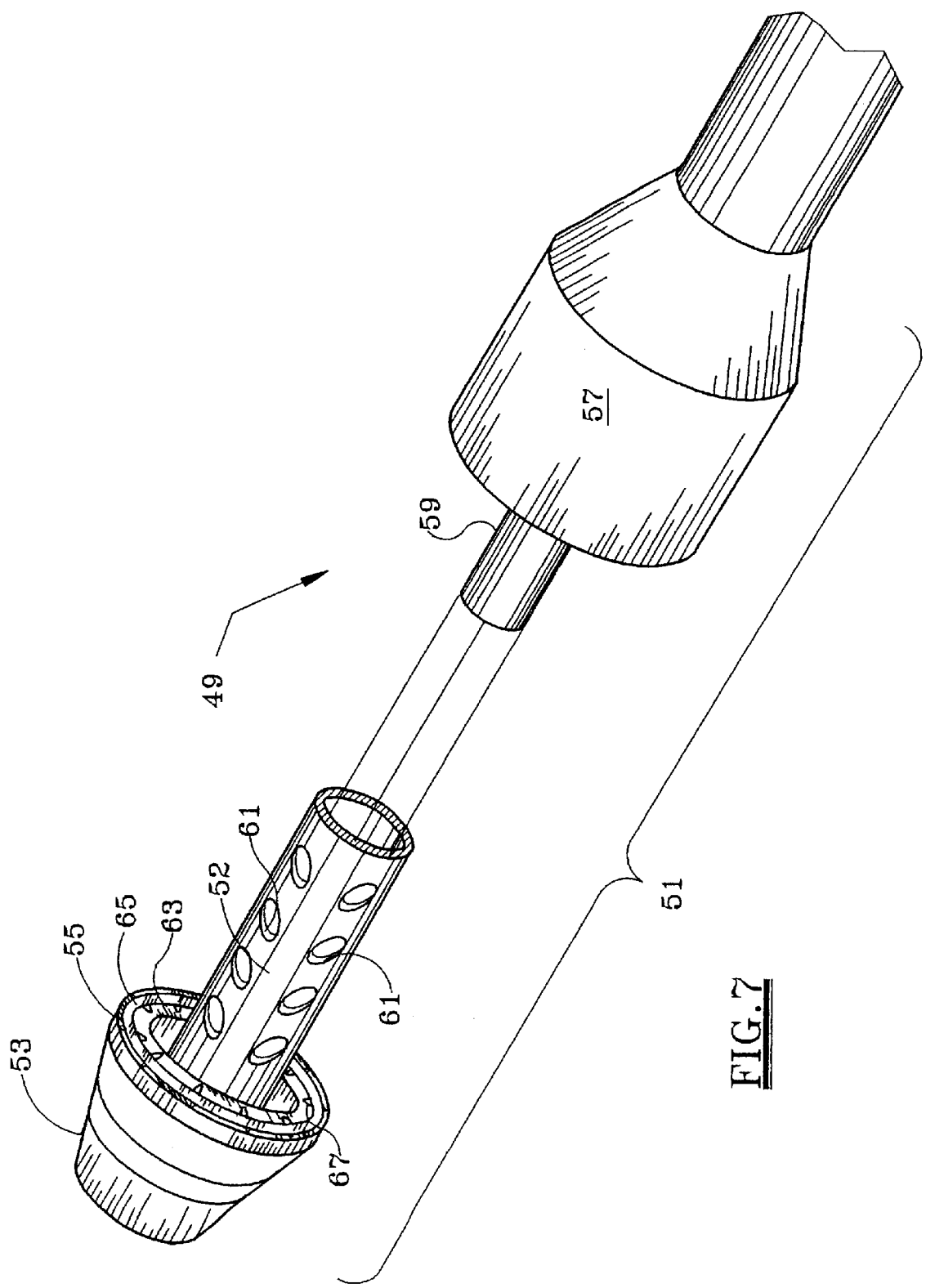

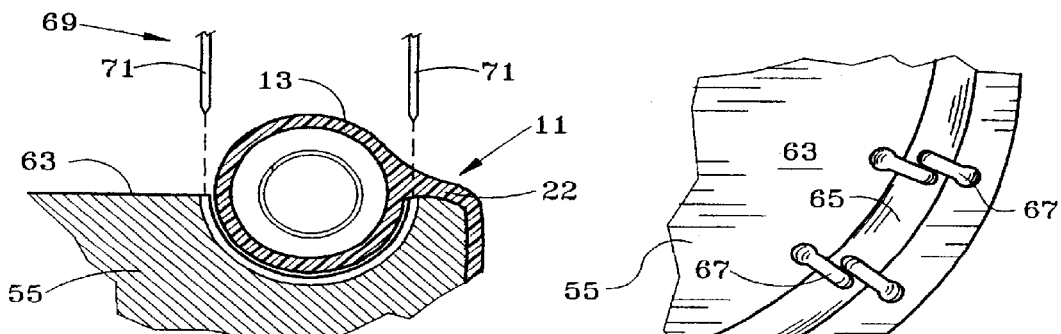
FIG.8A
FIG.8B
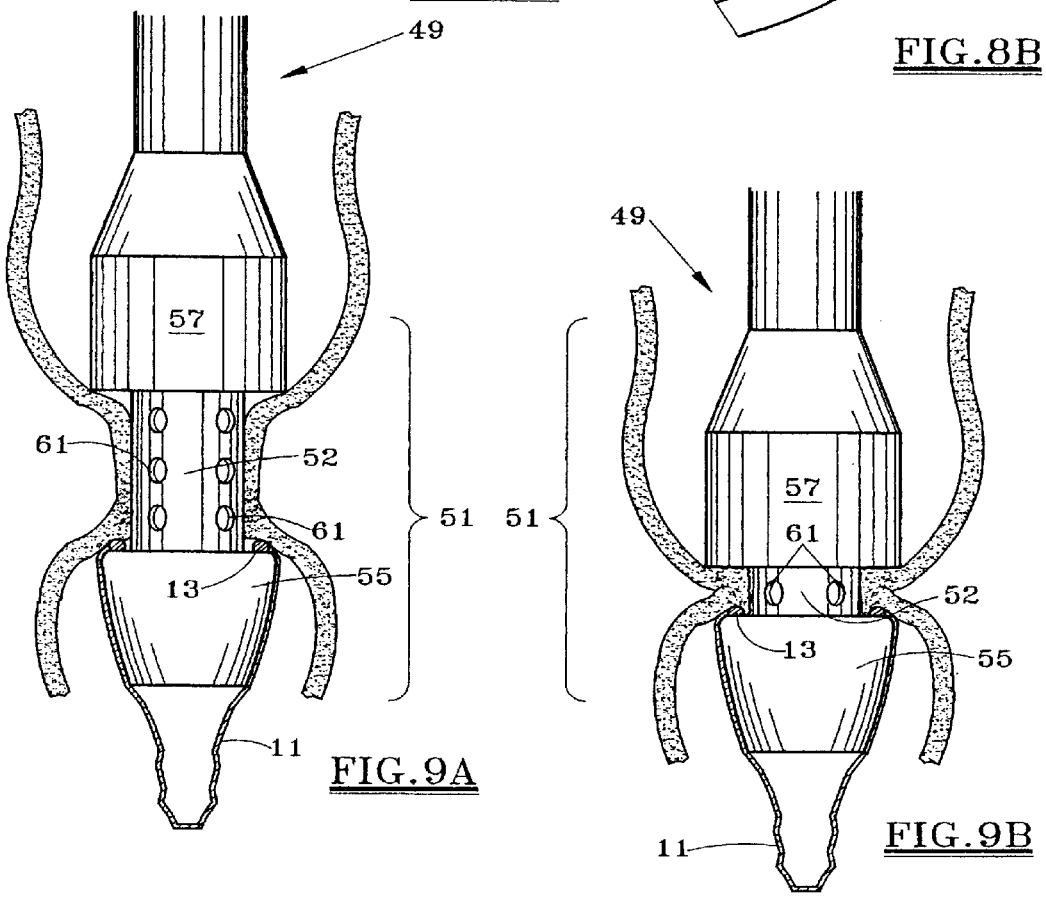
FIG.9A
FIG.9B

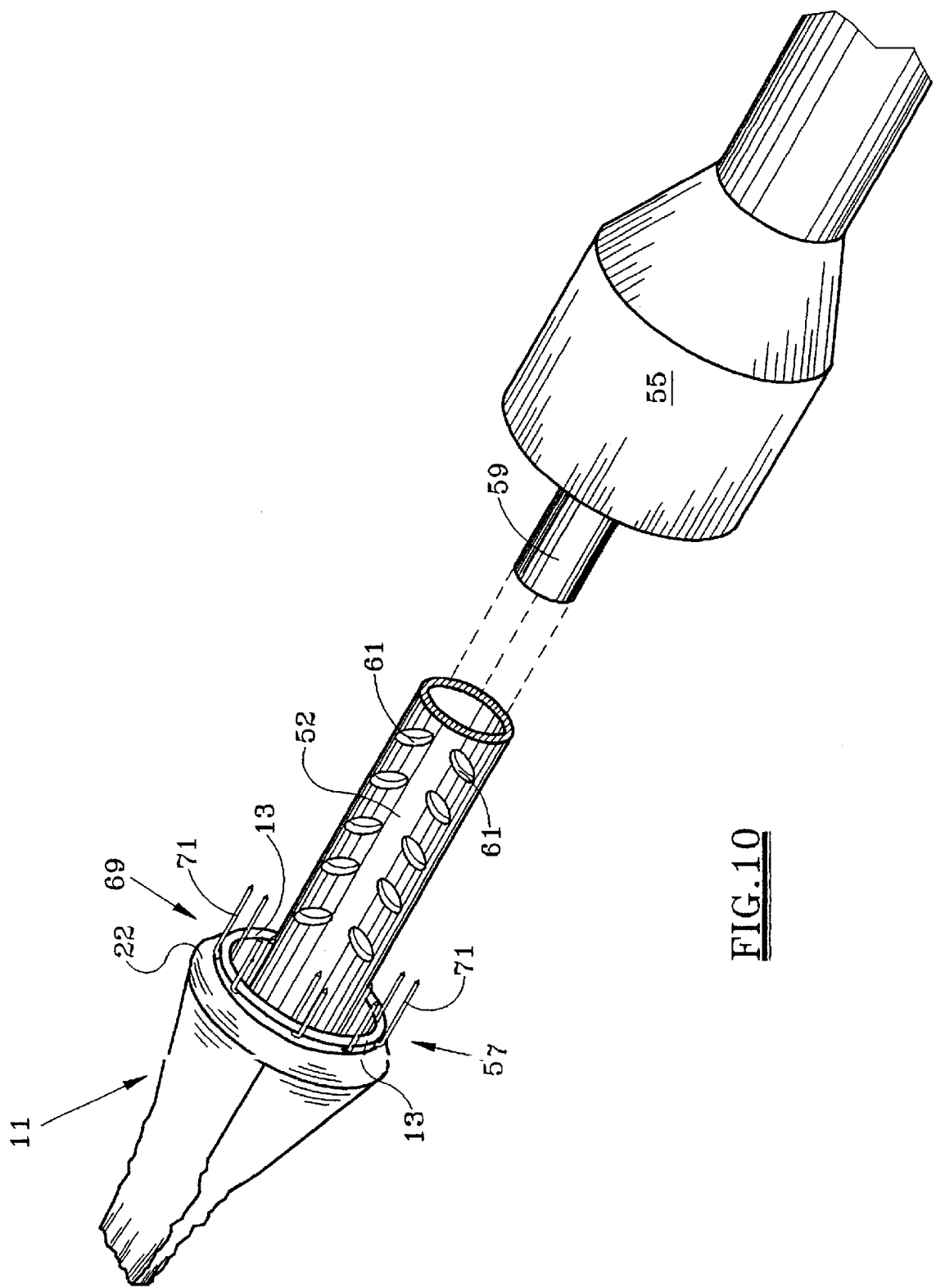

PERORALLY INSERTABLE GASTROESOPHAGEAL ANTI-REFLUX VALVE PROSTHESIS AND TOOL FOR IMPLANTATION THEREOF

FIELD OF THE INVENTION

This invention relates to a device and non-invasive surgical method for treating gastroesophageal reflux disease. More specifically, it relates to an anti-reflux valve prosthesis and associated instrumentation for its peroral placement and in situ fixing at the gastroesophageal junction, to prevent the reflux of gastric contents into the esophagus in the treatment of gastroesophageal reflux disease in a patient.

BACKGROUND OF THE INVENTION

Gastroesophageal reflux disease (GERD) is the commonest cause of dyspepsia, affecting some 30% of the United States adult population intermittently and some 10% on a continuous and troublesome basis. Gastroesophageal reflux disease produces heartburn, abdominal pain and regurgitation of acid-containing gastric contents into the esophagus and pharynx. It may also lead to alteration of the lining of the esophagus (Barrett's Esophagus), which may go on to produce esophageal cancer. Current methods of treating GERD include powerful antacid medication therapies and surgical interventions.

Medication therapy with powerful antacids is directed at treating the symptoms of GERD, and is necessarily not curative. Furthermore, medication-based therapies are not always fully effective, as reflux is not prevented and the esophagus may continue to be exposed to gastric content.

Surgical intervention typically involves either open surgery (performed through the abdomen or the chest) or laparoscopic surgery (performed through one or more incision access ports inserted through the abdominal wall), and the re-sectioning of tissue or the implanting of a prosthetic device. Although surgical interventions can be curative, these treatments are seriously invasive and have the attendant risk of such procedures. Despite the risk, the field has been motivated to provide solutions to the GERD problem, which has resulted in the development of a number of surgically implantable anti-reflux valve prosthetic devices. Prior anti-reflux valve prostheses are essentially one-way valves implanted at the gastroesophageal junction using open or laparoscopic surgery. The implanted prosthesis allows normal swallowing to take place in an orthograde manner while preventing the reflux of gastric contents from the stomach into the esophagus.

Examples of surgically implanted esophageal anti-reflux valve prostheses include the devices of: Godin (U.S. Pat. No. 5,314,473) which discloses a one-way, anti-return valve comprising a flattened tubular part associated with an annular fixing element; and Reich (U.S. Pat. No. 4,846,836) which discloses a bi-directional valve and housing for similar purposes. These devices were developed to be inserted into the gastro-esophageal junction via open or laparoscopic surgery and fixed there. The purpose was to permit the unidirectional passage of ingested materials into the stomach while preventing the reflux of gastric content of the stomach into the esophagus. Typically, these devices require suturing or other means to fix them to the tissue of the esophagus.

Generally, all of these prior devices and methods require surgical invasion of a body cavity and breach of the body membrane in some fashion (e.g., open surgery or laparoscopy) in order to accomplish their utility. However, such invasive surgical interventions are too frequently complicated by problems such as stricture formation, "gas bloat," or recurrent symptoms of reflux disease. Additionally, the results obtained by gross surgical treatment can be technique-dependent and vary significantly from surgeon to surgeon.

In view of the preference for minimally invasive forms of surgery there is a need in the art for GERD treatments which can be fully accomplished without surgically compromising the integrity of a patient's body membrane. Applicant has invented a peroral procedure for the insertion and implantation of an anti-reflux valve prosthesis that can address this need. It benefits the field to have an alternative prosthetic device and method that can be practiced to position and fix an anti-reflux prosthesis in place in the esophagus without resort to surgical incision or laparoscopy.

SUMMARY OF THE INVENTION

The present invention relates to an anti-reflux valve prosthesis system for treating gastroesophageal reflux disease (GERD) in a patient, which does not require open or laparoscopic surgery to implant. The present invention provides for perorally inserting an anti-reflux valve prosthesis down the lumen of the esophagus, to the gastroesophageal junction, where it is fixed in place. The advantage of this system is that peroral insertion of such a valve eliminates the need for either open formal laparotomy, thoracotomy or a laparoscopic approach using multiple access ports. Peroral installation of an anti-reflux prosthesis has the potential benefits of reducing the trauma, morbidity and hospital stay associated with implantation of anti-reflux valve prostheses relative to other surgical techniques. Furthermore, a system permitting the implantation of a standardized anti-reflux valve in an accurate and reproducible manner has the potential for providing more consistent clinical results than can be achieved with other technique-dependent methods of treatment.

The prosthesis system comprises an anti-reflux valve prosthesis and a peroral implantation tool for positioning and fixing the prosthesis proximate the distal end of the esophagus of a patient being treated for GERD. The present invention provides a prosthesis that is self-anchoring, having a mounting ring preferably constructed of a memory material supporting an anti-reflux valve. The memory material allows the mounting ring to be acted upon and deformed, but to return to its original shape when the deformation force is removed. The mounting ring is deformed during installation, but automatically returns to its original ring shape upon release. Also, the mounting ring incorporates tissue anchors which fixably engage the adjacent lumenal tissue of the esophagus to hold the prosthesis in place after installation. An anti-reflux valve is supported by the mounting ring. The anti-reflux valve is a normally closed, compliant one-way valve integral with the mounting ring. A variety of one-way valve types are practicable in the present invention by one of ordinary skill in the art. These include sleeve valves, monocuspid, bicuspid and tricuspid valves, hinged disk valves, double hinged valves and heart valves. Typically, the compliant part of a valve has structural supports to prevent the valve from inverting.

A feature of one installation tool is a removable compression collar for encircling the mounting ring and holding it in a compressed condition and for releaseably housing the prosthesis during positioning and prior to implantation. The compression collar is integral with one end of an overtube. The overtube is of a smooth and optionally flexible construction. The distal end of the overtube receives and holds the prosthesis in a compressed configuration during positioning of the prosthesis in the lumen of the esophagus. A further feature of the installation tool is a hollow stylet tube indwelling and slidable in the length of the overtube from the prosthesis at the distal end of the overtube to the handle at the proximal end of the overtube. At its distal end, the stylet is fitted with a normally deflated balloon which is inflatable by passing a gas or liquid (under appropriate pressure) through the hollow of the stylet tube and into the balloon. The deflated balloon is positioned and disengaged from the overtube in concert with the prosthesis. After disengagement, the balloon is inflated to exert pressure on the inside surface of the mounting ring of the prosthesis. The recovery of the memory material of the released mounting ring and the force exerted by the inflated balloon cause the tissue anchors of the mounting ring to engage with the lumenal tissue of the esophagus.

Another aspect of the present invention is a method for using the above tool to implant an anti-reflux valve prosthesis in a patient with GERD. In operation, a compressed prosthesis, housed in the compression collar of the implantation tool, is inserted down the esophagus of an anesthetized patient. When the prosthesis is in a proper position for implantation in the esophagus, the stylet and overtube are slidably positioned so as to disengage the overtube and compression collar from the compressed prosthesis while holding it in position. Upon disengagement, the prosthesis is allowed to autoexpand into position. Then the balloon feature of the stylet is inflated to positively engage the tissue anchor features of the prosthesis with the tissue of the esophagus. After the prosthesis is anchored in position, the balloon is deflated and the implantation tool is removed from the patient.

Another aspect of the present invention is an anti-reflux valve prosthesis system having an implantation tool that uses a circular surgical stapler to anchor an anti-reflux valve prosthesis in place in a patient's esophagus. The prosthesis is fixed in position by stapling a mounting ring integral with a one-way valve to the lumen wall of the esophagus. The stapler is accomplished by adapting any of a number of circular surgical staplers known in the art (such as in U.S. Pat. No. 5,445,644 to Pietrafitta et al., U.S. Pat. No. 5,411,508 to Bessler, and U.S. Pat. No. 5,104,025 to Main et al. which are hereby incorporated herein by reference) to include the vacuum tissue engagement means of the present invention.

In this embodiment, the installation tool has a tubular body having a length and outside diameter appropriate for passage through the mouth and down the esophagus. A substantially typically circular surgical stapler is mounted on the distal end of this tubular device. The stapler is comprised of four major features: (1) a head for dispensing and driving staples, (2) an anvil for receiving and bending staple points, (3) a tissue engager for engaging and holding lumenal tissue in an annular space between the head and anvil, and (4) a prosthesis holder for juxtaposing the mounting ring of a prosthesis with the engaged lumenal tissue. The relationship of these features is designed for the driving of staple points through the lumenal tissue and the mounting ring to fixably engage the two by then bending the staple points closed against the anvil. Typically, the head contains a series of staples which can be driven by activation of a handle operated outside the patient's mouth to drive the staples through the esophageal tissue to engage the mounting ring of the prosthesis. Force supplied to these staples drives them through the esophageal tissue, the mounting ring and against an anvil which bends the staples into a closed configuration to fix the tissue with the mounting ring.

The tissues to be stapled are drawn between the head and the anvil, by suction applied to a tubular member disposed between the head and anvil. Once the tissue is drawn between the head and anvil, activation of the handle of the tool sets the staples to permanently fix prosthesis in position in the esophagus. Withdrawal of the tool leaves the prosthesis permanently implanted in the esophagus. There the prosthesis will prevent reflux from occurring. The suspension ring is constructed of an appropriate material of sufficient strength and long term durability to enable the device to be permanently fixed in situ.

The present invention also provides a kit for treating gastroesophageal reflux disease comprising an autoclaveable container containing the prosthesis system described, and optional instructions for its use.

The valve prosthesis of the present invention is constructed of known materials, biologically inert and resistant to the media of stomach content. The prosthesis comprises a mounting ring and integral anti-reflux valve. The anti-reflux valve is an easy-opening one-way valve, implanted so that ingested materials may pass through it in an orthograde direction without significant impediment to their passage. The valve is normally closed, and the pressure differential between the stomach and the esophagus and between the abdominal and thoracic cavities act to maintain closure of the valve.

The mounting ring is typically made of a memory material (such as a nickel titanium alloy, spring steel, or suitable plastic). Similar devices, but without the incorporation of an anti-reflux valve, are known in the art and have been used in the treatment of strictures due to esophageal cancer. The memory material of the mounting ring typically is encased or encapsulated in a suitable biologically and chemically compatible or inert material such as silicone or the like.

In one embodiment of the prosthesis, the mounting ring (from which the valve is suspended) has an outwardly disposed, axial array of tissue anchors, typically, barbed spikes. When the mounting ring is properly positioned in the esophagus, the tissue anchors are implanted into the lumen wall of the esophagus, to fix the mounting ring/valve combination in place. The prosthesis (combination mounting ring and valve) is implanted using an implantation tool described above.

In a further aspect of the present invention, a prosthesis comprises an anti-reflux valve housed inside a cylindrical device made of a memory material which can be fixed in the distal esophagus. Such cylindrical devices have been used (without the incorporation of a valve prosthesis) in the treatment of strictures due to esophageal cancer. An example of such a device is the WALLSTENT® esophageal endoprosthesis (Schneider USA, Inc.). These devices typically comprise a cylinder of memory metal in close contact with a sleeve of suitable material, such as silicone. The prosthesis is inserted perorally and positioned using an adaptation of the usual tool used for installing such devices. The prosthesis is fixed in place by the expansion of the cylindrical device housing the anti-reflux valve.

BRIEF DESCRIPTION OF THE DRAWINGS

FIGS. 2A and 2B show self-mounting anti-reflux valve prostheses having (A) a single row array of tissue anchors and (B) a double rowed array of tissue anchors radially disposed and projecting outwardly from the mounting ring.

FIGS. 3A and 3B are perspective views of an alternative prosthesis of the present invention (A) showing the mounting ring having a single row array of tissue anchors or staple points projecting axially from the mounting ring wherein the staple crosspieces are substantially tangential with respect to the mounting ring, and (B) showing a partially cut-away view of the mounting ring.

FIGS. 4A and 4B are perspective views of an alternative prosthesis of the present invention (A) showing the mounting ring having a double rowed array of staple points or tissue anchors projecting axially from the mounting ring wherein the staple crosspieces are transverse to the mounting ring so that a pair of respective staple points on either end of each crosspiece are disposed on opposite sides of the mounting ring, and (B) showing a cut-away view of the mounting ring.

FIGS. 5A and 5B are views of the memory material of a mounting ring shown in the normally open position (A) and in the compressed position (B).

FIG. 6A is a cross-sectional view of the distal end of the implantation tool showing the relationship of the valve prosthesis, held in a compressed configuration by the collar portion of the overtube, with the balloon and stylet in pre-release position.

FIG. 6B is a side view of the distal end of the implantation tool showing the relationship of the array of radial tissue anchors to the collar portion of the overtube, and the balloon/stylet combination inside the prosthesis.

FIG. 6C is a partial cross-sectional view of the distal end of the implantation tool showing the relationship of the elements immediately upon disengagement of the collar from the prosthesis/stylet combination.

FIG. 6D is a partial cross-sectional view of the prosthesis installation site in a patient's esophagus showing the balloon in an inflated condition and the engagement of the tissue anchors with the tissue of the esophagus.

FIG. 6E is a cross-sectional view of the anti-reflux valve prosthesis in place in a patient's esophagus after the balloon has been deflated and the insertion tool removed.

FIGS. 7 is a perspective expanded view of the distal end of a circular surgical stapler for implantation of a valve prosthesis tool showing the relationship of the stapler head to the anvil and the location of tissue engagement vacuum ports.

FIG. 8A is a cross-sectional view of a section of a stapler anvil showing the relationship of the detent, staple bending notch, the prosthesis mounting ring and skirt to the staple points.

FIG. 8B is a top view of the same section of the stapler anvil as FIG. 8A, but without the prosthesis, showing the relationship of the detent channel and the staple bending notches in the surface of the anvil.

FIG. 9A shows the relationship of the head and anvil of the circular surgical stapler after the staple head and anvil are approximately opposed or spaced apart and receiving the tissue of the esophageal lumen wall upon the application of a vacuum to the stapler assembly.

FIG. 9B shows the relationship of the head and anvil of the circular surgical stapler after the staple head and anvil are approximately opposed or spaced apart for compressing and stapling the received tissue of the lumen wall to the mounting ring of the prosthesis.

FIG. 10 is a perspective view of the surgical stapler showing the stapler head in the distal position with a valve prosthesis received on the head.

DETAILED DESCRIPTION OF THE INVENTION

As exemplified by the figures, the present invention provides a peroral prosthesis system for treatment of gastroesophageal reflux disease (GERD) in a patient comprising an anti-reflux valve prosthesis, and a peroral implantation tool for perorally inserting and positioning the valve prosthesis at the distal end of the lumen of the esophagus, and implanting or fixing the valve prosthesis to the lumen wall.

Figure 1A:
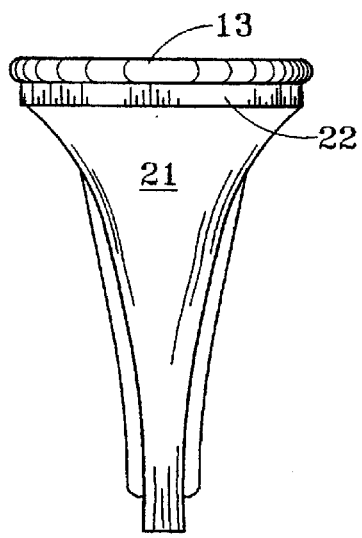
FIGS. 1A, 1B and 1C are views of an anti-reflux valve prosthesis of the present invention showing the side, front and top of the prosthesis, respectively.
Figure 1B:
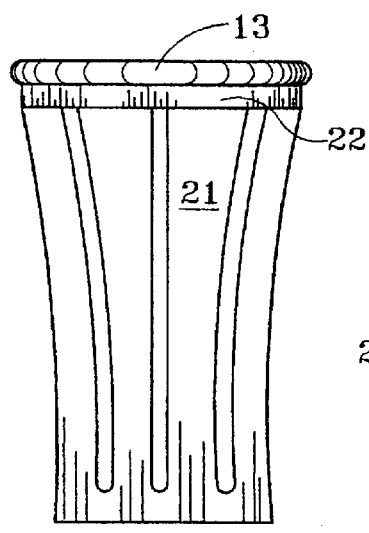
Figure 1C:
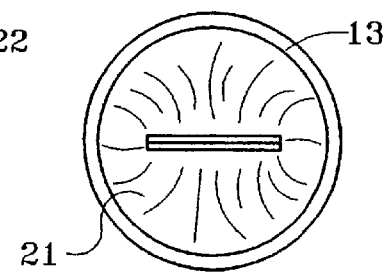

Referring to FIG. 1, in one preferred embodiment, the anti-reflux valve prosthesis 11 of the present invention has a mounting ring 13. The inner diameter or central bore of the ring 13 is compatible with orthograde passage of ingested (or swallowed) material through the lumen of the esophagus. A one-way, anti-reflux valve 21 depends from the mounting ring 13 by a valve skirt 22 which is a short section of material connecting the mounting ring 13 with the cylinder end of the valve 21. The one-way anti-reflux valve 21 permits the easy passage of ingested material through the bore of the mounting ring 13 in one direction, while impeding the reflux of stomach content through the bore of the mounting ring 13 in the other direction. A suitable anti-reflux valve 21 for practicing the present invention is a typical mitral or bicuspid type valve of a half-flaftened cylindrical shape. Such a shape is easily suspended from the mounting ring 13 by its cylindrical end. Other valves, as previously disclosed, are practicable in the present invention by the ordinary skilled artisan.

The prosthesis 11 is generally constructed of and/or coated with physiologically inert materials such as polymeric, ceramic or metallic materials. In a preferred embodiment, the exterior surface of the prosthesis has a textured surface to promote adhesion and facilitate anchoring of the prosthesis to the adjacent esophageal wall, while the interior surfaces are smooth and/or hydrophobic to facilitate the orthograde passage of food and liquids therethrough. Thus, the exterior of the prosthesis can be made of or coated with microporous ceramic such as apatite, for example, hydroxyapatite, open- or closed-cell elastomer foams such as polyurethane, for example, or the like. Smooth materials for the interior surfaces of the prosthesis generally include silicone, polytetrafluoroethylene and the like.

Figure 2A:
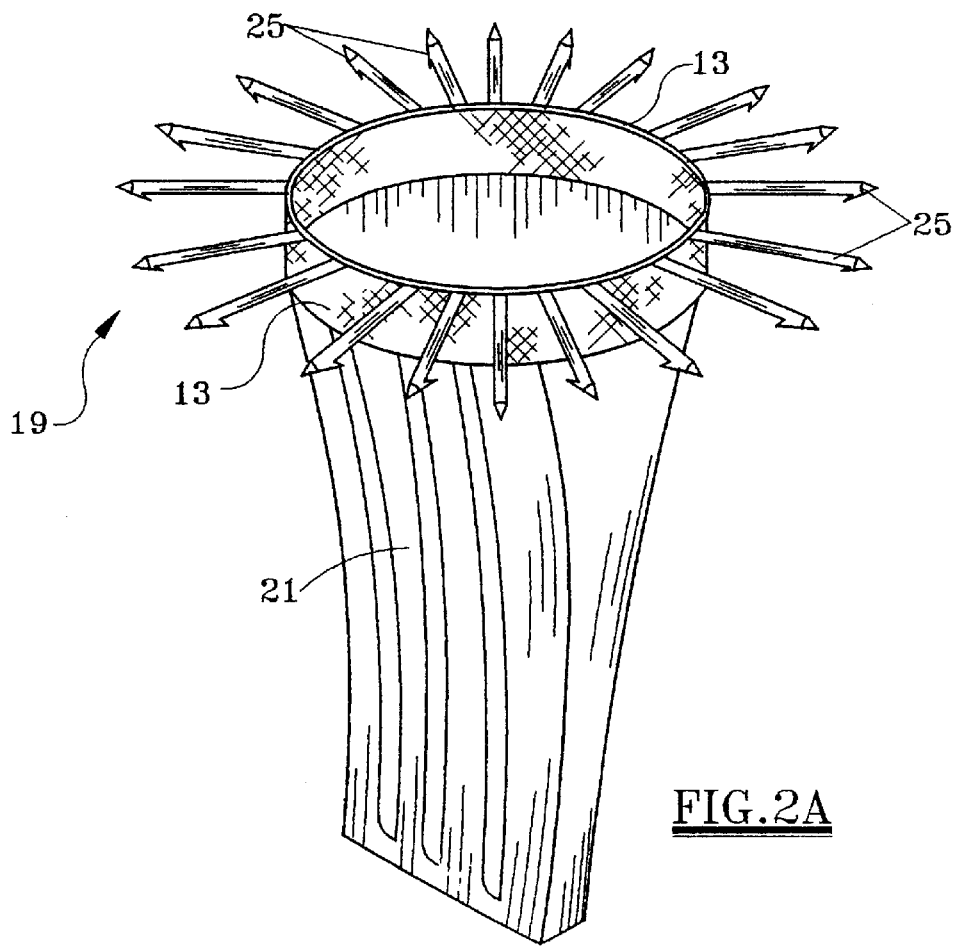
Figure 6A:
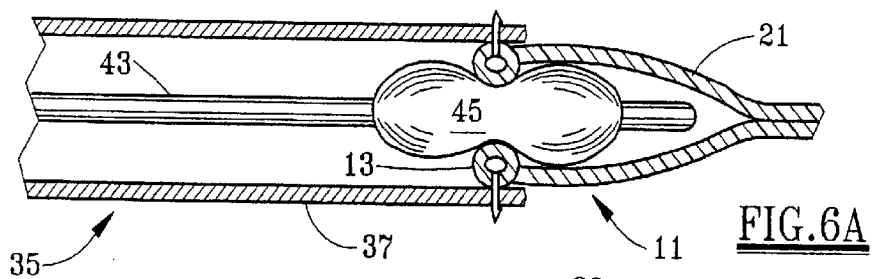
FIGS. 6A–6E are a series of cross-sectional views showing elements of the insertion tool and their relationship to a valve prosthesis in various stages of the implantation of the prosthesis in the lumen of a patient's esophagus.
Figure 6B:
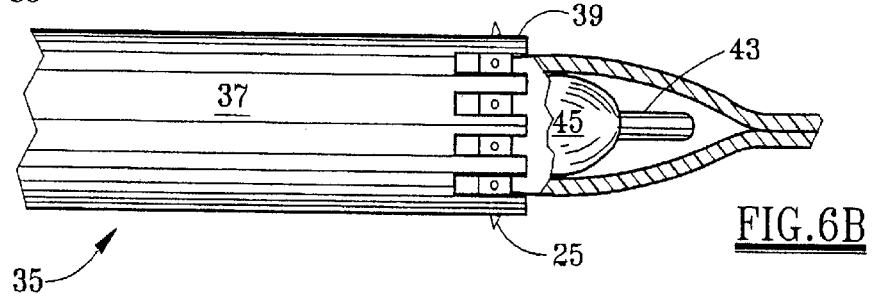
Figure 6C:
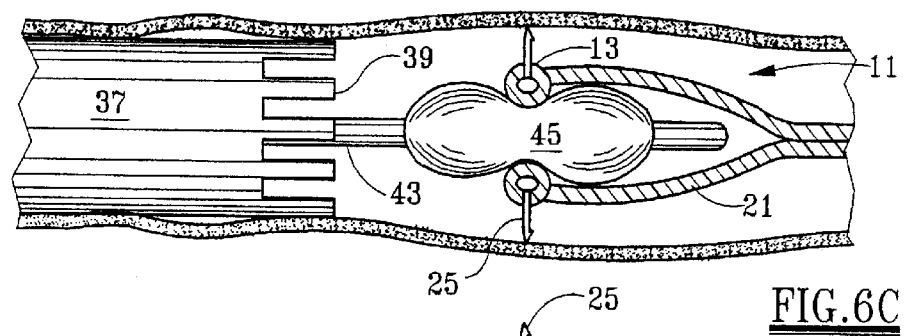
Figure 6D:
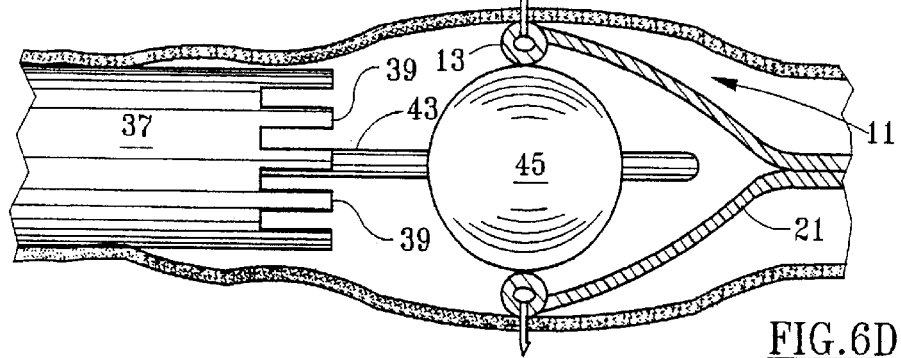
Figure 6E:
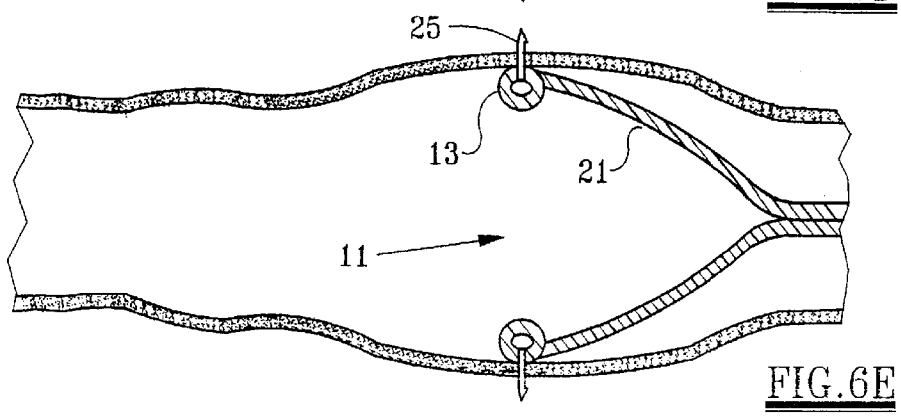

Referring to FIGS. 2A–2B, the prosthesis 11 also includes a tissue anchor array 19 for fixing the mounting ring 13 of the prosthesis 11 to the lumen of the esophagus. The tissue anchor array 19 extends radially outward from the axis of the ring 13. In this embodiment, the tissue anchor array 19 is comprised of barbed spikes 25 for piercing and engaging the lumen wall of the esophagus. The tissue anchor array 19 can be comprised of at least eight spikes or points, but can have as many as forty or more spikes or points arrayed in a plurality of rows. As shown in FIGS. 3B, 4B, 5A and 5B, the mounting ring 13 is comprised of a memory material 15 shown in the form of a helical spring, and preferably includes a compliant and biologically inert coating 17 such as silicone or polytetrafluoroethylene. The memory material 15 and coating 17 form a combination which may be acted upon by a force and stretched or compressed from its original shape, but automatically returns substantially to the original shape upon removal of the force. FIGS. 5A and 5B show a memory material 15 of a mounting ring 13 comprising a "key-ring" configuration in the normally open position (A) and in the compressed position (B).

Referring to FIGS. 6A–6E, in one preferred embodiment, the prosthesis system of the present invention includes an implantation tool 35 for holding and perorally inserting a prosthesis 11 down the lumen of a patient's esophagus to a position proximate the gastroesophageal junction, and fixing the prosthesis 11 to the lumen wall. In one preferred embodiment, the tool 35 comprises a flexible overtube 37, of a construction and length suitable for peroral insertion into the esophagus. At one end, the overtube 37 has an integral compression collar 39 and at the other end a handle (not shown). A compression collar 39 is integral to the collar end 39 of the overtube 37, and provides a means for releaseably receiving the ring 13 of the prosthesis 11 in a compressed configuration. A hollow stylet 43 is slidably contained (or indwelling) in the length of the overtube 37 from end to end. At the collar 39 of the overtube 37, the stylet 43 has a balloon 45 attached. The bladder of the balloon 45 communicates with the hollow of the stylet 43, and the balloon 45 is inflatable by pressurizing the hollow of the stylet 43 with a gas or liquid inserted into the hollow from the handle end of the tool 35.

Referring to FIG. 7, in another preferred embodiment, an alternative implantation tool 49 of the present invention comprises an intralumenal circular surgical stapler 51, for holding and perorally inserting a prosthesis 11 down the lumen of an esophagus and fixing the prosthesis 11 to the lumen wall. The intralumenal stapler 51 has a prosthesis holder 53 and is connected to a vacuum source (not shown) via a perforated tube 52. The stapler 51 comprises an anvil 55 and a head 57 having surfaces which are opposed, separated and positionable relative to each other by means of a central, hollow draw shaft 59 connectedly disposed between them. The section of the draw shaft 59 between the head 57 and anvil 55 is supplied with through vacuum ports 61. The vacuum ports 61 communicate the hollow of the shaft 59 with the gap between the anvil 55 and head 57. Further, the hollow of the draw shaft 59 communicates with a vacuum source outside the patient, which serves to apply a vacuum to the hollow of the draw shaft 59 which is communicated to the annular space between the anvil 55 and head 57 by means of the ports 61.

Referring to FIGS. 8A and 8B, the anvil 55 has a circular anvil surface 63 inset with a detent channel 65 for receiving, holding and releasing, upon application of appropriate force, the mounting ring 13 of the prosthesis 11. The anvil 55 also has a plurality of notches 67 radially disposed in pairs, one on either side of the detent 65 for receiving and bending a staple point 71 of a staple 69. The stapler head 57 dispenses staples 69 radially across the mounting ring 13. The dispensed staples 69 pierce the periphery or valve skirt 22 of the prosthesis 11 with at least one point 71 of each staple. Each point 71 then engages an opposing notch 67 on the anvil surface 63, which bends the staple point 71 closing it about the mounting ring 13.

Generally, when the prosthesis 11 is being inserted and positioned in the esophagus, the stapler 51 is configured with the anvil 55 and head 57 in a closed position. In the closed position, the anvil 55 and head 57 are drawn closely together upon the draw shaft 59 to enclose the mounting ring 13 of the prosthesis 11. When the prosthesis 11 is in position for installation, the stapler 51 is configured in the fully open position, with the anvil 55 and head 57 spaced widely apart on the draw shaft 59. Referring to FIGS. 9A and 9B, in operation, when the prosthesis 11 has been positioned in the esophagus at the implantation site using tool 49, and the stapler 51 is configured in the fully open position (as in FIG. 9A), a vacuum is applied to the interior of the draw shaft 59 (see FIG. 7). The vacuum is communicated through the perforated tube 52 via the vacuum ports 61. The vacuum pressure at the site draws the lumenal tissues of the esophagus between the head 57 and anvil 55 of the stapler 51, and up against the tube 52 (see FIG. 9A).

When the tissues have been drawn up against the tube 52, the anvil 55 and head 57 are carefully redrawn on shaft 59 to an intermediate position containing an appropriate thickness of tissues in the gap between the head 57 and anvil 55. In this configuration, the lumenal tissue is juxtaposed with the mounting ring 13 of the prosthesis 11 and positioned for stapling. An appropriate gap contains a sufficient thickness of tissue in which to implant the prosthesis 11, and still be properly spanned by the staples 69 to engage the notches 67 of the anvil 55 when driven by the head 57.

It should be noted that the stapler head 57 does not have to dispense the staples 69 used to fix the ring 13 to the lumenal tissue. Alternatively, the staples 57 are integral with and radially disposed across the mounting ring 13 of the prosthesis 11 with their points 71 disposed generally parallel to the axis of the prosthesis 11, as shown in FIGS. 3A and 3B and 4A and 4B. In this embodiment, the head 57 is disposed on the distal end of the tool 49 and has a surface inset with the detent 65 for releaseably receiving the mounting ring 13 and staples 69 combination. The combination of the ring 13 and staples 69 is held in a configuration to engage the notches on the anvil surface. After the staples 69 have been set and bent against the anvil 55, tnus implanting the mounting ring 13 in the lumen, the prosthesis 11 is released from the detent 65 by the force of the removal of the tool 49 from the esophagus.

In a preferred embodiment, the present invention provides a minimally invasive method of surgically treating gastroesophageal reflux disease in a patient comprising the steps of inserting the present peroral prosthesis system down the lumen of the esophagus of a patient to be treated; positioning the valve prosthesis 11 of the system at an appropriate position in the esophagus approximate the gastroesophageal junction of the patient; operating the tool and fixing the valve prosthesis 11 in place in the esophagus of the patient; removing the implantation tool 51 of the peroral prosthesis system from the esophagus of the patient; and leaving the prosthesis 11 in situ in the lumen of the esophagus to treat the patient's gastroesophageal reflux disease.

In a further preferred embodiment, the present invention is a kit for treating gastroesophageal reflux disease in a patient comprising a sterile or sterilizable package (not shown) containing the peroral prosthesis system of the present invention and preferably accompanied with instructions for its handling and use.

Figure 11:
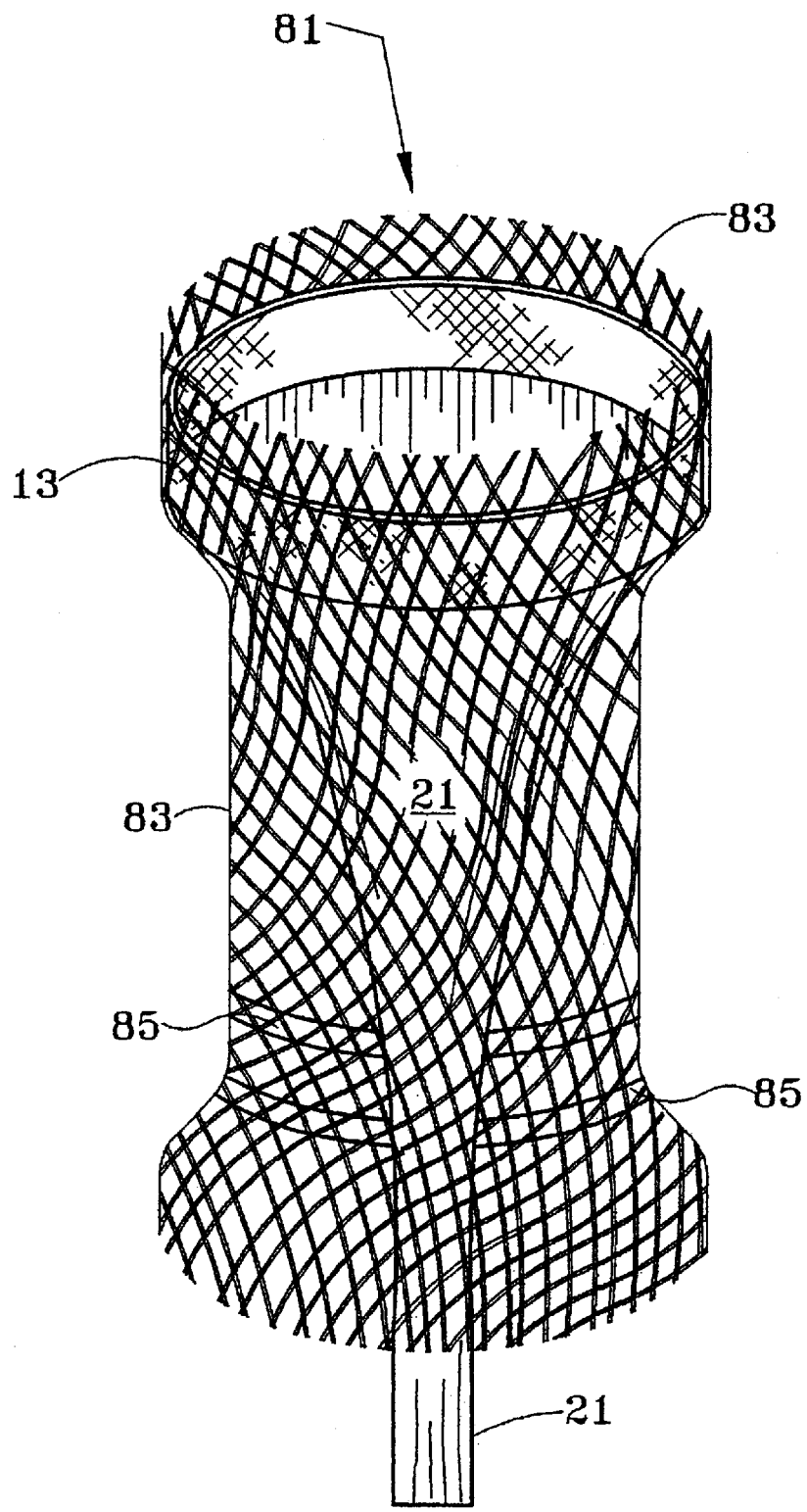
FIG. 11 is a view of a self-anchoring valve prosthesis showing a metal mesh memory material housing containing an anti-reflux valve.

Referring to FIG. 11, in another preferred embodiment, the present invention provides a valve prosthesis 81 comprising a cylindrical housing 83 constructed of a memory material, in this example a metal mesh. Suspended within the interior of the cylindrical housing is an one-way valve 21. The one-way valve 21 has a mounting ring 13 which is fixed to the interior wall of the housing. Preferably, the mounting ring 13 is constructed of a compressible memory material. A feature of this embodiment is the optional anti-inversion supports 85, one end of which is fixed to the lower portion of the valve 21 and the other end of which is fixed to the interior wall of the cylindrical housing 83. The supports 85 prevent the valve 21 from inverting.

While the above description contains many specifics, these should not be construed as limitations on the scope of the invention, but rather as exemplifications of preferred embodiments thereof. Many other variations are possible, which would be obvious to one skilled in the art. Accordingly, the scope of the invention should be determined by the scope of the appended claims and their equivalents, and not just by the embodiments.

What is claimed:

1. A peroral prosthesis system for treatment of gastroesophageal reflux disease in a patient comprising:

an anti-reflux valve prosthesis comprising:

a mounting ring made of an expandable, compressible memory material;

an anchor comprising staples for fixing the mounting ring in the lumen of the esophagus; and a one-way valve depending from the mounting rings for allowing orthograde passage of swallowed material, and impeding the passage of gastric content; and a peroral implantation tool for perorally inserting and positioning the prosthesis at a distal end of the lumen of an esophagus, and fixing the prosthesis to the lumen wall of the esophagus, comprising an intralumenal, circular surgical stapler, having an annular space connected to a vacuum source and a prosthesis holder.

2. The system of claim 1 wherein the stapler comprises a head, an anvil axially positionable from the head, a perforated tube for drawing the lumen of the esophagus between the head and the anvil, and a holder for disengageably receiving a prosthesis mounting ring.

3. The system of claim 2 wherein the stapler comprises:

a stapler head for dispensing and driving staples;

an anvil having a circular surface opposing the stapler head, and inset with a channel for receiving and holding the mounting ring, and a plurality of notches radially disposed in pairs on opposite sides of the channel for receiving and bending staple points; and staples disposed in the head with points positioned across the mounting ring to engage the notches on the anvil surface.

4. The system of claim 2 wherein the stapler comprise:

a stapler head for dispensing and driving staples, having a surface inset with a channel for receiving and holding a mounting ring;

staples, having staple points radially disposed across the mounting ring; and an anvil, having a circular surface opposing the stapler head, and a plurality of notches radially disposed in pairs for receiving and bending the staple points.

5. The system of claim 2 wherein the stapler comprises:

a stapler head for driving staples, having a surface inset with a channel for receiving and holding a mounting ring;

a mounting ring, held in the channel, and having staple points integrally incorporated therein and radially projecting from the mounting ring; and an anvil, having a circular surface opposing the stapler head, and a plurality of notches disposed for receiving and bending the staple points.

6. An anti-reflux valve prosthesis comprising:

a mounting ring;

an array of at least one row of tissue anchors presenting at least 8 points extending outward from the mounting ring, in the direction substantially parallel to the esophagus the anchors having staple points for engaging the lumen wall of an esophagus and fixing the mounting ring in the lumen of the esophagus; and a one-way valve depending from the mounting ring, for allowing orthograde passage of swallowed material, and impeding the passage of gastric content.

7. The peroral prosthesis system of claim 1 wherein the prosthesis implantation tool comprises:

a shaft having a distal stapler end and a proximal handle end;

the intralumenal, circular surgical stapler connected to the distal end of the shaft, the stapler having a head, an anvil axially positionable from the head, the vacuum source adapted for drawing the lumen of the esophagus into the annular space between the head and the anvil, and the prosthesis holder adapted for disengageably receiving the mounting ring;

a handle connected to the proximal end of the shaft, for receiving a vacuum and for manipulating and operating the stapler; and the shaft having internally disposed means for connecting the operation of the handle with the operation of the stapler.

8. The system of claim 7 wherein the stapler further comprises:

a stapler head for dispensing and driving staples;

an anvil having a circular surface opposing the stapler head, and inset with a channel for receiving and holding the mounting ring, and a plurality of notches radially disposed in pairs on opposite sides of the channel for receiving and bending staple points; and staples disposed in the head with points positioned across the mounting ring to engage the notches on the anvil surface.

9. The system of claim 7 wherein the stapler further comprises:

a stapler head for dispensing and driving staples, having a surface inset with a channel for receiving and holding a mounting ring;

staples, having staple points radially disposed across the mounting ring; and an anvil, having a circular surface opposing the stapler head, and a plurality of notches radially disposed in pairs for receiving and bending the staple points.

10. The system of claim 7 wherein the stapler further comprises:

a stapler head for driving staples, having a surface inset with a channel for receiving and holding a mounting ring;

the mounting ring, held in the channel, and having staple points integrally incorporated therein and radially projecting from the mounting ring; and an anvil, having a circular surface opposing the stapler head, and a plurality of notches disposed for receiving and bending the staple points.

11. A minimally invasive method for surgically treating gastro-esophageal reflux disease in a patient with the system of claim 1 comprising the steps of:

perorally inserting the prosthesis received in a distal end of the implantation tool into an esophagus;

positioning the prosthesis adjacent to an esophageal junction;

fixing the prosthesis in place in the esophagus of the patient;

removing the implantation tool from the esophagus; and leaving the valve prosthesis in situ to treat gastroesophageal reflux disease.

12. A kit for treating gastroesophageal reflux disease in a patient comprising:

a package;

the peroral prosthesis system of claim 1 housed within the package; and optionally, instructions for use of the peroral prosthesis system.

13. The kit of claim 12 wherein the package and contents are sterile.

14. The anti-reflux valve prosthesis of claim 6 wherein the mounting ring comprises a helical spring and a biologically inter coating.

15. The anti-reflux valve prosthesis of claim 14 wherein the anchors comprise a crosspiece between pairs of staple points and wherein the crosspieces are disposed within the coating substantially tangentially with respect to the mounting ring.

16. The anti-reflux valve prosthesis of claim 14 wherein the anchors comprise a crosspiece between pairs of staple points and wherein the crosspieces are disposed transversely through the coating so that a pair of respective staple points on either end of each crosspiece are disposed on opposite sides of the coating.

17. The invention of any of claim 1, 14, 15, 16 wherein the valve is selected from sleeve valves.

* * * * *